(12) United States Patent
Farnsworth

(10) Patent No.: US 8,072,224 B2
(45) Date of Patent: Dec. 6, 2011

(54) METHODS FOR PREDICTING THE FUTURE PERFORMANCE OF FUEL CELL STACKS AND INDIVIDUAL FUEL CELLS

(75) Inventor: Jared Michael Farnsworth, Sacramento, CA (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 793 days.

(21) Appl. No.: 12/185,286

(22) Filed: Aug. 4, 2008

(65) Prior Publication Data

US 2010/0026307 A1    Feb. 4, 2010

(51) Int. Cl.
*H01M 10/44* (2006.01)
*H01M 8/00* (2006.01)
*G01N 27/416* (2006.01)

(52) U.S. Cl. ........ 324/433; 320/101; 324/426; 429/430; 429/452

(58) Field of Classification Search .................. 320/101, 320/134, 135, 136, 137, 138, 161, 162; 324/425, 324/426, 432, 433; 429/400, 452, 430, 431, 429/432
See application file for complete search history.

(56) References Cited

U.S. PATENT DOCUMENTS

| | | | |
|---|---|---|---|
| 5,763,113 A | 6/1998 | Meltser et al. | |
| 5,929,594 A * | 7/1999 | Nonobe et al. | 320/104 |
| 6,388,421 B2 * | 5/2002 | Abe | 320/104 |
| 6,411,098 B1 | 6/2002 | Laletin | |
| 6,469,512 B2 | 10/2002 | Singh et al. | |
| 6,762,587 B1 * | 7/2004 | Barbetta | 320/116 |
| 6,847,188 B2 * | 1/2005 | Keskula et al. | 320/101 |
| 7,087,332 B2 | 8/2006 | Harris | |
| 7,659,018 B2 * | 2/2010 | Aoyagi et al. | 429/431 |
| 7,816,884 B2 * | 10/2010 | Wake et al. | 320/101 |
| 2003/0206021 A1 * | 11/2003 | Laletin et al. | 324/426 |
| 2004/0028977 A1 | 2/2004 | Pickup et al. | |
| 2004/0257087 A1 | 12/2004 | Murakami | |
| 2005/0214606 A1 * | 9/2005 | Higashionji et al. | 429/23 |
| 2006/0194082 A1 | 8/2006 | Tucker et al. | |
| 2008/0076012 A1 * | 3/2008 | Lienkamp et al. | 429/65 |
| 2009/0092882 A1 * | 4/2009 | Kjeang et al. | 429/34 |

FOREIGN PATENT DOCUMENTS

JP    02051866    2/1990

* cited by examiner

*Primary Examiner* — Edward Tso
*Assistant Examiner* — Alexis Boateng
(74) *Attorney, Agent, or Firm* — Dinsmore & Shohl LLP

(57) ABSTRACT

Method embodiments for analyzing the future performance of a fuel cell stack comprise the steps of: a) generating a first polarization curve data by experimentally measuring the voltage of a fuel cell stack across a current range at a first interval; b) dividing the current range into a plurality of discrete current ranges; c) calculate an average voltage value for each discrete current range; d) fitting all average voltage values to produce a first average polarization curve; e) conducting steps a) through d) at a second interval to produce a second average polarization curve; f) comparing the first average polarization curve to the second polarization curve to calculate the drop in voltage and thereby the fuel cell stack degradation; and g) utilizing the calculated drop in voltage between the first and second polarization curves to predict the polarization of the fuel cells at future time intervals.

16 Claims, 3 Drawing Sheets

METHODS FOR PREDICTING THE FUTURE PERFORMANCE OF FUEL CELL STACKS AND INDIVIDUAL FUEL CELLS

TECHNICAL FIELD

Embodiments of the present invention are generally directed to methods of predicting the future performance of electrochemical devices, and are specifically directed to predicting the future performance of fuel cell stacks and individual fuel cells therein in order to ascertain fuel cell degradation and/or the need for replacement of a fuel cell stack or individual fuel cells.

BACKGROUND

As a background, current fuel cells, fuel cell stacks, battery cells, and battery pack monitoring methods analyze individual cells or overall stack/pack performance for real time performance characteristics, but do not give an indication of future performance. Accordingly, improved real time methods of detecting future performance of fuel cells, which would determine when fuel cells should be replaced, are desirable.

SUMMARY

In accordance with one embodiment, a method of analyzing future performance for a fuel cell stack is provided. The method comprises: a) generating a first polarization curve by experimentally measuring the voltage of a fuel cell stack across a current range at a first interval, b) dividing the current range into a plurality of discrete current ranges, c) obtaining an average voltage value for each discrete current range, d) fitting all average voltage values onto a first average polarization curve, e) conducting steps a) through d) at a second interval to produce a second average polarization curve, f) comparing the first average polarization curve to the second polarization curve to measure the drop in voltage from the first interval to the second interval, wherein the voltage drop corresponds to an amount of degradation of the fuel cell stack, and g) utilizing the measured drop in voltage between the first and second polarization curves to predict the polarization of the fuel cells at future time intervals.

According to another embodiment, a method of analyzing future performance for individual fuel cells in a fuel cell stack is provided. The method comprises: a) generating a first polarization curve by experimentally measuring the voltage of each individual cell in a fuel cell stack across a current range at a first interval, b) dividing the current range into a plurality of discrete current ranges, c) obtaining an average voltage value for each discrete current range, d) e) selecting a current value, f) obtaining the voltage value for each individual fuel cell at that selected current value, g) conducting steps a) through f) at a second interval to produce a second set of voltage values for each individual fuel cell at that selected current value, h) comparing the first individual fuel cell voltages to the second individual fuel cell voltages to measure the drop in voltage from the first interval to the second interval, wherein the voltage drop corresponds to an amount of fuel cell degradation, and i) utilizing the measured drop in voltage between the first and second individual fuel cell voltages to predict the polarization of the individual fuel cells at future time intervals.

According to yet another embodiment, fuel cell performance may be predicted for both the fuel stack and individual fuel cells using a combination of the above embodiments.

These and additional objects and advantages provided by the embodiments of the present invention will be more fully understood in view of the following detailed description, in conjunction with the drawings.

BRIEF DESCRIPTION OF THE DRAWINGS

The following detailed description of specific embodiments of the present invention can be best understood when read in conjunction with the drawings enclosed herewith. The drawing sheets include.

Figure 1A:
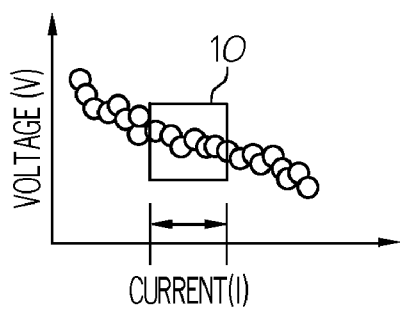
FIGS. 1A-1D illustrates a graphically a model used to predict the future performance of a fuel cell stack according to one or more embodiments of the present invention.

The embodiments set forth in the drawings are illustrative in nature and not intended to be limiting of the invention defined by the claims. Moreover, individual features of the drawings and the invention will be more fully apparent and understood in view of the detailed description.

DETAILED DESCRIPTION

Figure 3:
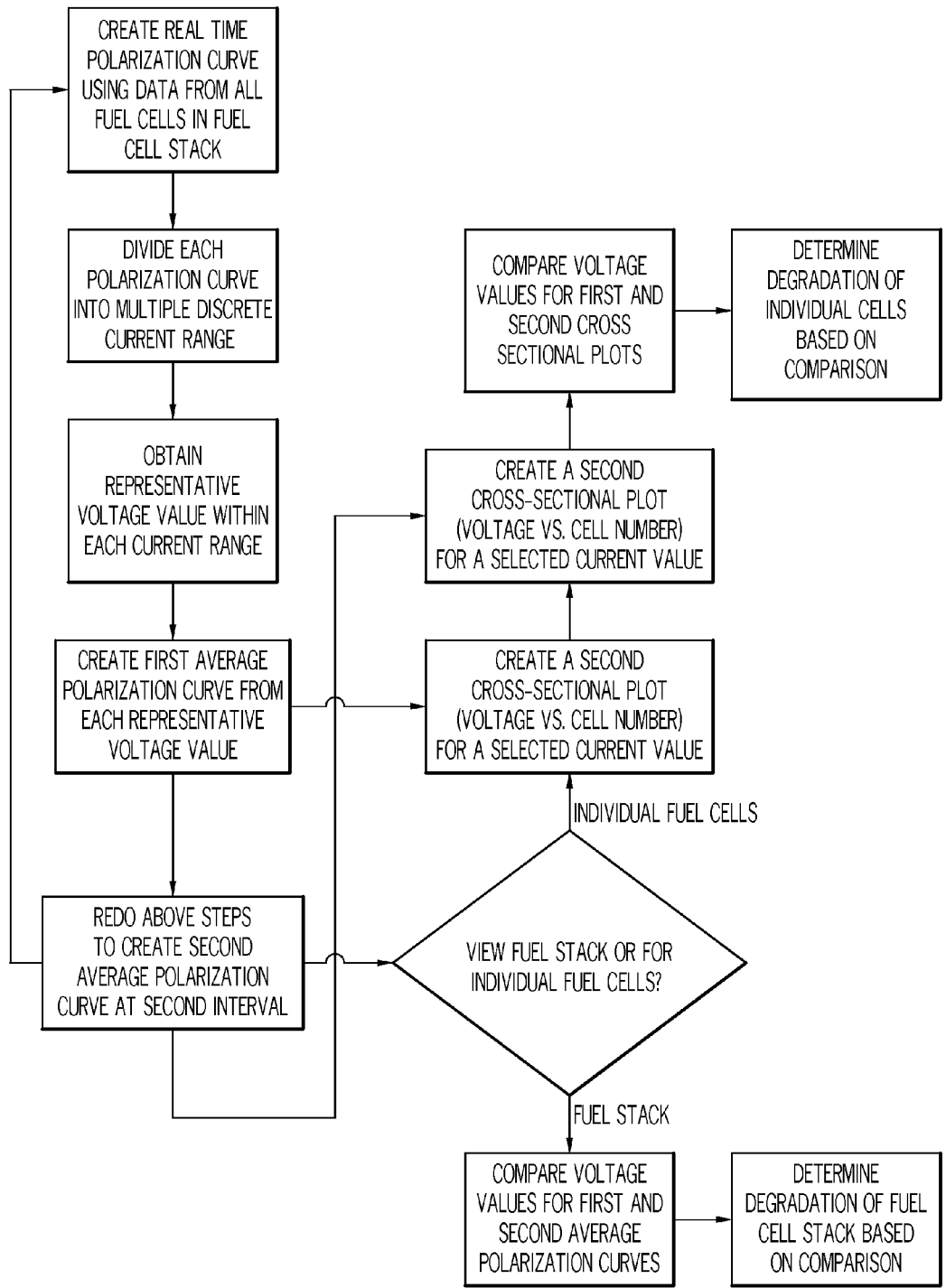
FIG. 3 is a flow chart illustrating a model used to predict the future performance of a fuel cell stack (as illustrated in FIGS. 1A-1D) and/or individual fuel cells (as illustrated in FIGS. 2A-2E) disposed therein according to according to one or more embodiments of the present invention.

Referring generally to the flow chart of FIG. 3, embodiments of the present invention are directed to methods of analyzing the future performance of fuel cell stacks and the individual fuel cells inside the fuel cell stack. Referring generally to the Figures, the methods of the present invention use a model and algorithm, which incorporates real-time polarization data from fuel cell stacks and fuel cells therein. Although the description of the present invention centers on fuel cell stacks, it is contemplated that this invention is operable for other electrochemical devices (e.g., batteries).

Referring to FIG. 1A, a polarization curve is generated by monitoring the fuel cell stack and all individual cells therein at a first interval. A polarization curve is a plot of voltage as a function of current, which helps characterize the performance of electrochemical devices such as fuel cells and batteries. A vehicle processor may generate the curve, and the data could be analyzed by the vehicle and via an external processor. By evaluating the voltage drop, the polarization curve can be an indication of the efficiency, power performance, physical characteristics, etc. As stated above, the polarization data may be obtained at a first interval, which may be the first time the fuel cell is used or at a subsequent point after first use. The interval may be chosen by hours of operation, for example, the first polarization interval is at 1000 hr, and the second polarization interval is at 2000 hr.

Figure 1B:
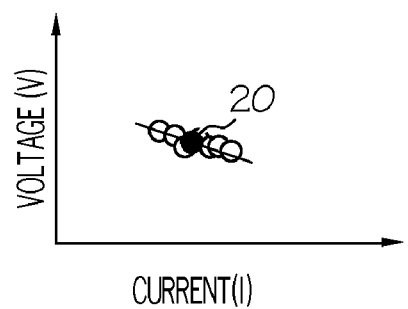
Figure 1C:
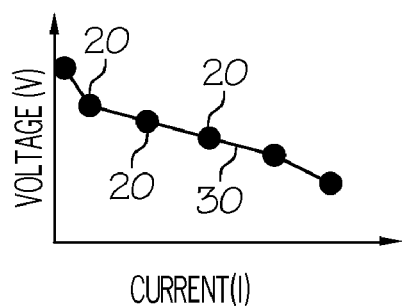

After the first polarization curve is obtained, the present method selects discrete current ranges 10 as shown in FIG. 1A. Referring to FIG. 1B, all of the voltage values within each selected current range are fit to a line through a best fit algorithm or another suitable technique. Via the best fit analysis, a voltage value 20 is selected for each discrete current range 10. As shown in FIG. 1B, this voltage value 20 may be the midpoint of the best fit line. Referring to FIG. 1C, the voltage values 20 for all of the discrete ranges 10 are used to produce a first average polarization curve 30 at a first interval. The current ranges selected may equal fractions of the total curve.

Figure 1D:
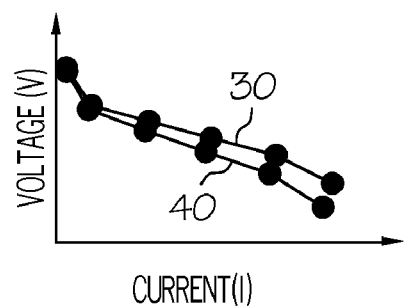

Referring to FIG. 1D, the future performance of the fuel cell stack may be predicted by generating a second average polarization curve 40 at a second interval. The second interval may include any time after the first interval. In some instances, the second interval may occur one or more years after the first interval. To generate the second average polarization curve 40, the same process steps as described above and as illustrated in FIGS. 1A through 1C are performed. Although the present figures show only two curves, multiple average polarization curves at multiple intervals are contemplated herein.

Referring to FIG. 1D, the first polarization curve 30 and the second polarization curve 40 is plotted on the same graph. As shown in the embodiment of FIG. 1D, the fuel cell stack at the first interval (top curve) will usually demonstrate higher voltage at each current value then a fuel stack at the second interval (bottom curve), in part due to degradation of the fuel cell. By comparing the curves, the user may determine the amount of degradation in the fuel cell stack from the first interval to the second interval through the decrease in voltage. Based on this voltage decrease, the rate of degradation, the efficiency of the fuel stack as well as other performance metrics may be evaluated. Based on the voltage drop, the voltage and performance of the fuel cell stack may be predicted at later time intervals through extrapolation. Predicting the future voltage and performance can instruct the user on when to replace the fuel cell stack.

When determining when a fuel cell and/or a fuel cell stack needs to be maintained, replaced, etc, the present model may set a predefined threshold value that defines an acceptable degree of voltage produced or an acceptable voltage drop. If a voltage of a fuel cell or fuel cell stack is predicted to meet or exceed the predefined threshold, the model will instruct the user when and what should be maintained, replaced, etc In one exemplary embodiment, a technician may download the average polarization curve data at first and second time intervals, and then analyze the data (e.g., by running a macro). If any cell is predicted to fall below standards before the next maintenance period, thereby causing performance issues, the technician may then decide to perform maintenance, replace the cell, etc before the next maintenance period.

Figure 2A:
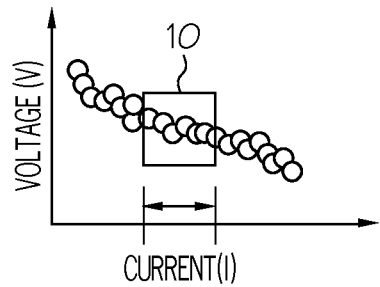
FIGS. 2A-2E illustrate graphically a model used to predict the future performance of the individual fuel cells of a fuel cell stack according to one or more embodiments of the present invention.
Figure 2B:
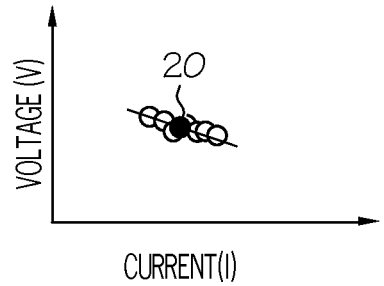
Figure 2C:
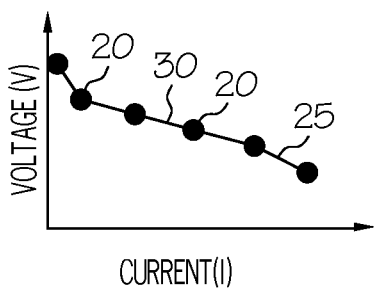
Figure 2D:
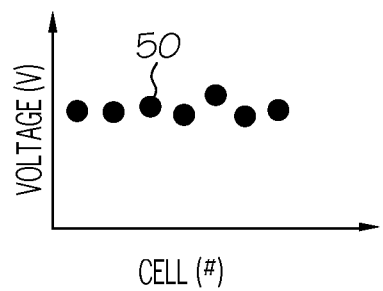
Figure 2E:
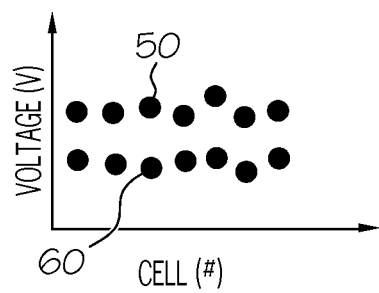

In addition to predicting the future performance of the fuel cell stack, the present model may also predict the future performance of each fuel cell in the fuel cell stack as shown in FIGS. 2A through 2E. Similar to the process above, a first polarization curve and at least one average voltage values from the polarization curve are generated as shown in FIGS. 2A-2B. Also, as shown in FIG. 2C, a first average polarization curve is generated. At this point, the model may select at least one value 25 on the first average polarization curve. In one embodiment, a values may equal fractions of the total curve (e.g., ¼, ½, ¾, and end). Next, referring to FIG. 2D, the voltage of each individual fuel cell is determined based on the current associated with selected value 25. The voltage values for each individual fuel cell may be obtained from the polarization curve data that was used to populate the polarization curve of FIG. 2A. These voltage values are demonstrated as a first individual cross sectional plot 50 shown in FIG. 2D. The cross sectional plot 50 displays the voltage for each fuel cell in the stack at the selected current value 25. To determine the degradation of each individual fuel cell, individual fuel cell voltage values are obtained by redoing the steps illustrated in FIGS. 2A-2D at a second interval and demonstrated in a second cross sectional plot 60. Referring to FIG. 2E, the cell voltages illustrated in the first individual cross sectional plot 50 and the second individual cross sectional plot 60 may be compared to measure the voltage drop and thereby the degradation from the first interval to the second interval. Like the methodology for the fuel cell stack described above, the present model may determine the performance and voltage of the individual fuel cells at future time intervals.

In a further embodiment, the model may locate individual fuel cells having a drop in voltage between the first and second intervals that is greater than an acceptable threshold value. Corrosion within the fuel cell stack may impact some individual fuel cells more than others, thus pinpointing fuel cells which are degrading at a more rapid rate is desirable. Replacing one cell inside a fuel cell stack is generally more economical than replacing the entire stack.

As shown in the flow chart of FIG. 3, the model of the present invention may simultaneously predict the future performance of the fuel cell stack and the individual fuel cells therein. Like the methods above, first and second average polarization curves are created via steps 310 through 350. As shown in step 360, the model may determine the future performance of the fuel cell stack or the individual fuel cells therein via the first and second average polarization curves. As shown in steps 370 and 372, the degradation of the fuel cell stack may be determined by comparing the first and second average polarization curves. In steps 380 and 382, the first and second individual cross-sectional plots may be obtained from the first and second average polarization curves. Based on the first and second individual cross-sectional plots, the degradation of each individual fuel cell may be determined as illustrated in steps 384 and 386. Referring generally to FIG. 3, the model may evaluates whether one or more individual fuel cells need to be replaced, or the entire stack as a whole needs to be replaced.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method of analyzing future performance for a fuel cell stack comprising:
    a) generating a first polarization curve by experimentally measuring the voltage of a fuel cell stack across a current range at a first interval;
    b) dividing the current range into a plurality of discrete current ranges;
    c) obtaining an average voltage value for each discrete current range;
    d) fitting all average voltage values onto a line or curve, the curve being defined as a first average polarization curve;
    e) conducting steps a) through d) at a second interval to produce a second average polarization curve;
    f) comparing the first average polarization curve to the second polarization curve to measure the drop in voltage from the first interval to the second interval, wherein the voltage drop corresponds to an amount of degradation of the fuel cell stack; and
    g) utilizing the measured drop in voltage between the first and second polarization curves to predict the voltage values of the fuel cells at future time intervals.

2. The method of claim 1 further comprising replacing a fuel cell stack when the drop in voltage between the first and second polarization curve exceeds an acceptable threshold value.

3. The method of claim 1 wherein the average voltage value is obtained by creating a best fit line for the voltage values within each discrete current range, and selecting a point on the best fit line as the average voltage value.

4. The method of claim 1 wherein the average voltage value may be located from the best fit line.

5. The method of claim 1 wherein the first interval is the initial use of the fuel cell stack.

6. The method of claim 1 wherein the second interval is one or more years after the first interval.

7. The method of claim 1 further comprising conducting steps a) through d) at a third time interval to produce a third average polarization curve.

8. A method of analyzing future performance for individual fuel cells in a fuel cell stack comprising:
   a) generating a first polarization curve by experimentally measuring the voltage of each individual cell in a fuel cell stack across a current range at a first interval;
   b) dividing the current range into a plurality of discrete current ranges;
   c) obtaining an average voltage value for each discrete current range;
   d) fitting all average voltage values onto a line or curve, the curve being defined as a first average polarization curve;
   e) selecting at least one value on the first average polarization curve;
   f) obtaining the voltage value for each individual fuel cell based on the current associated with the selected value;
   g) conducting steps a) through f) at a second interval to produce a second individual cross sectional plot;
   h) comparing the first individual cross sectional data to the second individual cross sectional data to calculate the drop in voltage from the first interval to the second interval, wherein the voltage drop corresponds to an amount of fuel cell degradation; and
   i) utilizing the measured drop in voltage between the first and second cross-sectional data to predict the voltage values of the individual fuel cells at future time intervals.

9. The method of claim 8 further comprising locating individual fuel cells having a drop in voltage between the first and second intervals more than a threshold value.

10. The method of claim 8 further comprising replacing a fuel cell inside the fuel cell stack when the drop in voltage between the first and second intervals exceeds an acceptable threshold value.

11. The method of claim 8 wherein the average voltage value is obtained by creating a best fit line for the voltage values within each discrete current range, and selecting a point on the best fit line as the average voltage value.

12. The method of claim 8 wherein the average voltage value may be located from the best fit line.

13. The method of claim 8 wherein the first interval is the initial use of the fuel cell stack.

14. The method of claim 8 wherein the second interval is one or more years after the first interval.

15. The method of claim 8 further comprising conducting steps a) through g) at a third time interval to produce a third second individual cross sectional data.

16. A method of analyzing future performance for a fuel cell stack comprising:
   a) generating a first polarization curve by experimentally measuring the voltage of each individual fuel cell of a fuel cell stack across a current range at a first interval;
   b) dividing the current range into a plurality of discrete current ranges;
   c) obtaining an average voltage value for each discrete current range;
   d) fitting all average voltage values onto a line or curve, the curve being defined as a first average polarization curve;
   e) conducting steps a) through d) at a second interval to produce a second average polarization curve;
   f) comparing the first average polarization curve to the second polarization curve to measure the drop in voltage from the first interval to the second interval, wherein the voltage drop corresponds to an amount of degradation of the fuel cell stack;
   g) utilizing the calculated drop in voltage between the first and second polarization curves to predict the polarization of the fuel cells at future time intervals;
   h) selecting at least one value on the first average polarization curve;
   i) obtaining the voltage value for each individual fuel cell based on the current associated with the selected value;
   j) obtaining the voltage value for each individual fuel cell at that selected current value at the second interval;
   k) comparing the first individual cross sectional data to the second individual cross sectional data to calculate the drop in voltage from the first interval to the second interval, wherein the voltage drop corresponds to an amount of fuel cell degradation; and
   m) utilizing the measured drop in voltage between the first and second cross-sectional data to predict the voltage values of the individual fuel cells at future time intervals.

* * * * *